United States Patent
Tsuda et al.

(10) Patent No.: US 9,063,087 B2
(45) Date of Patent: Jun. 23, 2015

(54) RADIATION DETECTOR SIGNAL PROCESSOR AND RADIATION DETECTOR PROVIDED THEREWITH

(75) Inventors: Tomoaki Tsuda, Kyoto (JP); Masanobu Sato, Kizugawa (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/386,310

(22) PCT Filed: Mar. 21, 2012

(86) PCT No.: PCT/JP2012/001950
§ 371 (c)(1),
(2), (4) Date: Sep. 18, 2014

(87) PCT Pub. No.: WO2013/140443
PCT Pub. Date: Sep. 26, 2013

(65) Prior Publication Data
US 2015/0041661 A1 Feb. 12, 2015

(51) Int. Cl.
*G01N 21/64* (2006.01)
*G01T 1/164* (2006.01)

(52) U.S. Cl.
CPC .............. *G01N 21/64* (2013.01); *G01T 1/1644* (2013.01); *G01T 1/1647* (2013.01)

(58) Field of Classification Search
CPC .... A61B 6/037; A61B 6/4258; G01T 1/1642; G01T 1/00; G01T 1/20; G01N 21/64

USPC ....................................................... 250/361 R
See application file for complete search history.

(56) References Cited

U.S. PATENT DOCUMENTS

| | | | | |
|---|---|---|---|---|
| 5,493,120 A | * | 2/1996 | Geagan | 250/363.02 |
| 5,585,637 A | * | 12/1996 | Bertelsen et al. | 250/363.03 |
| 5,646,408 A | * | 7/1997 | Goldberg et al. | 250/363.07 |
| 6,169,285 B1 | * | 1/2001 | Petrillo et al. | 250/369 |
| 7,071,474 B2 | | 7/2006 | Wong et al. | |
| 2012/0228484 A1 | * | 9/2012 | Burr | 250/252.1 |
| 2013/0299704 A1 | * | 11/2013 | Nakazawa | 250/362 |

OTHER PUBLICATIONS

International Search Report PCT/JP2012/001950 dated Apr. 24, 2012 with English translation.

* cited by examiner

*Primary Examiner* — Marcus Taningco
(74) *Attorney, Agent, or Firm* — McDermott Will & Emery LLP

(57) ABSTRACT

Disclosed is a radiation detector signal processor that allows accurate identification of a variation in fluorescence detection intensity. With a construction of the disclosure, the variation is obtainable in accordance with detection data (a peak value) of fluorescence and a specified number of light spread indicating how the fluorescence generated in a scintillator spreads spatially until reaching each of detecting elements. Such a construction allows accurate obtainment of the variation in the radiation detector in which the fluorescence is detected with a plurality of light detecting elements while spreading. A radiation detector is adjusted in accordance with the variation, achieving more accurate positional identification by the radiation detector.

8 Claims, 9 Drawing Sheets

Fig.14
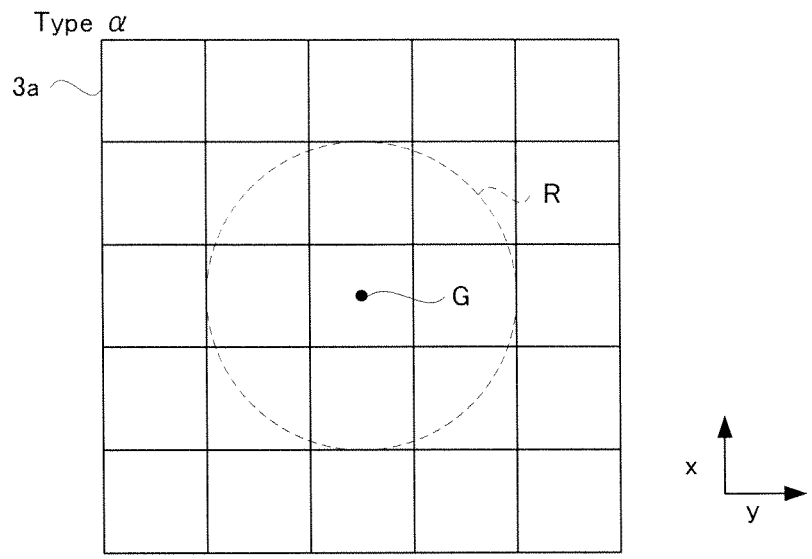
Fig.15
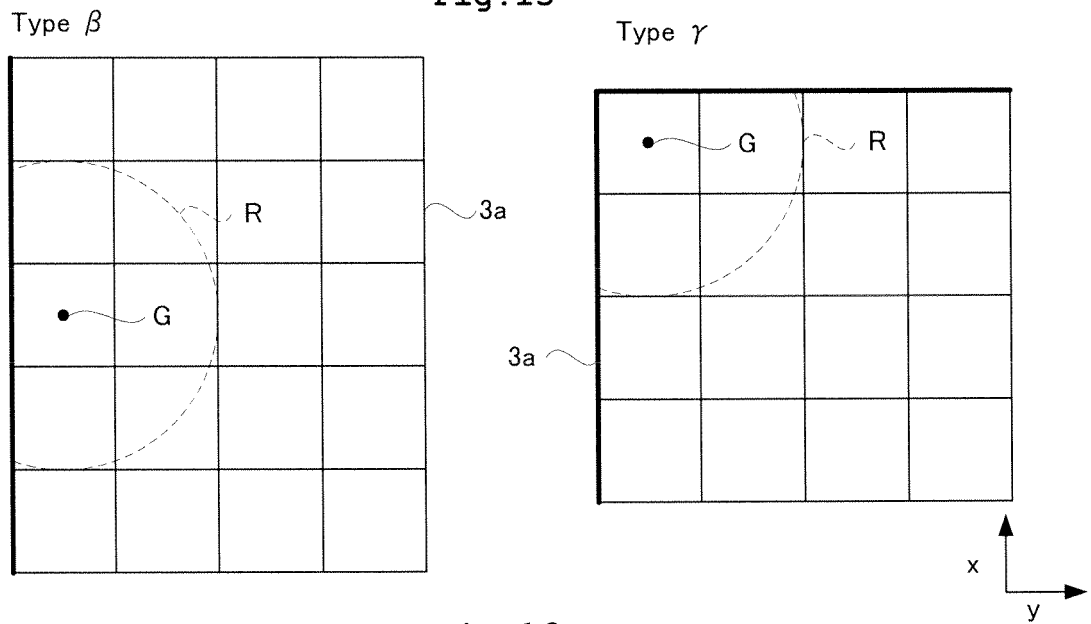
Fig.16

| b1 | b2 | b3 |
|----|----|----|
| b4 | b5 | b6 |
| b7 | b8 | b9 |

Prior art

RADIATION DETECTOR SIGNAL PROCESSOR AND RADIATION DETECTOR PROVIDED THEREWITH

RELATED APPLICATIONS

This application is the U.S. National Phase under 35 U.S.C. §371, of International Application No. PCT/JP2012/001950, filed on Mar. 21, 2012, the disclosures of which Applications are incorporated by reference herein.

TECHNICAL FIELD

The present invention relates to a radiation detector signal processor configured to correct detection signals of an annihilation radiation pair, and a radiation detector provided with the processor. More particularly, the present invention is directed to a radiation detector signal processor that allows correction of a detecting position of radiation, and a radiation detector provided with the processor.

BACKGROUND ART

The following describes a concrete construction of a currently-used positron emission tomography (PET) apparatus that images radiopharmaceutical distribution. The currently-used PET apparatus includes a detector ring having radiation detectors for detecting radiation arranged in a ring shape. The detector ring detects a pair of radiation (an annihilation radiation-pair) having opposite directions to each other and emitted from radiopharmaceutical within a subject.

Next, a construction of a radiation detector 51 is to be described. As illustrated in FIG. 23, the radiation detector 51 includes a scintillator 52 having scintillation counter crystals arranged three-dimensionally, and a light detector 53 configured to detect fluorescence from γ-rays absorbed into the scintillator 52. The radiation detector 53 has detection surfaces of light detecting elements 53a arranged in a two-dimensional matrix. The detection surface of the light detector 53 is optically connected to one surface of the scintillator 52. See U.S. Pat. No. 7,071,474.

Radiation entering into the scintillator 52 is converted into many photons to travel toward the light detector 53. Here, the photons travels through the scintillator 52 while spatially spreading to the detection surfaces of the light detector 53 arranged in a matrix. That is, many photons from fluorescence are split into many detecting elements 53a to be detected simultaneously.

The radiation detector 51 determines a position in the scintillator 52 where fluorescence is emitted using detection data of the fluorescence that is captured by a plurality of detecting elements 53a. That is, the radiation detector 51 determines a position of the center of gravity in a luminous flux of fluorescence on the detection surface by the detecting element 53a. The position of the center of gravity means a position where fluorescence has been generated. Data on the position is used when radiopharmaceutical within the subject is mapped.

PATENT LITERATURE

Patent Literature 1 U.S. Pat. No. 7,071,474A

SUMMARY OF INVENTION

Technical Problem

However, the currently-used construction has a following drawback. Specifically, a difference in property of the light detecting elements 53a of the light detector 53 may cause incorrect identification of a generating position of fluorescence.

The detecting elements 53a have different detection sensitivities. Specifically, even when fluorescence enters into two light detecting elements 53a at the same intensity, output data from the light detecting elements 53a does not always contain the fluorescence with the same intensity. When the generating position of the fluorescence is identified with such different detection sensitivities of the light detecting elements 53a, the identified generating position of fluorescence deviates from an actual generating position. This is because the generating position of fluorescence is determined from data indicating a fluorescence intensity outputted from each of the detecting elements 53a.

Upon shipment of the light detector 53, light intensities of the light detecting elements 53a can be controlled to be even. However, such a control is unsatisfactory for accurate identification of the position of fluorescence since a variation in detection sensitivity of fluorescence occurs upon manufacturing the radiation detector 51. Accordingly, the light detecting elements 53a have a variation in detection sensitivity of fluorescence although the light detecting elements 53a have even sensitivities. Such a variation derives from different portions of the scintillator 52 or the light guide 54 varied in its property or different conditions of connecting the elements to each other.

The present invention has been made regarding the state of the art noted above, and its object is to provide a radiation detector signal processor that allows accurate identification of a variation in fluorescence sensitivity, and a radiation detector provided with the processor.

SUMMARY

The present invention adopts the following construction for overcoming the above drawback. One aspect of the present invention discloses a radiation detector signal processor including a spectrum obtaining device configured to receive detection data from a radiation detector provided with a scintillator and a plurality of light detecting elements, and configured to obtain an energy spectrum of radiation corresponding to the detection data for each of the light detecting elements, the scintillator converting radiation into fluorescence, and the plurality of light detecting elements detecting an intensity of the fluorescence; a peak value obtaining device configured to obtain a peak value of the energy spectrum for each of the light detecting elements; and a variation obtaining device configured to obtain a variation in fluorescence detection intensity among the light detecting elements in accordance with the peak value and a specified number of light spread, the specified number indicating how the fluorescence generated in the scintillator spreads spatially until reaching each of the detecting elements.

Operation and Effect

The radiation detector signal processor according to one aspect of the present invention obtains the variation in fluorescence detection intensity among the light detecting elements of the radiation detector. With the construction of the present invention, the variation is obtainable in accordance with the detection data (the peak value) of the fluorescence and the specified number of light spread indicating how the fluorescence generated in the scintillator spreads spatially until reaching each of the detecting elements. Such a construction allows accurate obtainment of the variation in the radiation detector in which fluorescence is detected with a plurality of light detecting elements while spreading. The radiation detector is adjusted in accordance with the variation, achieving more accurate positional identification by the radiation detector.

It is more preferable in the radiation detector signal processor that the specified number of light spread is obtained by emitting radiation to the scintillator uniformly and detecting the radiation with each of the light detecting elements.

Operation and Effect

The above is a concrete construction of the radiation signal processor according to the present invention. As noted above, the specified number of light spread is obtained by emitting radiation to the scintillator uniformly. This achieves obtainment of light spread within the scintillator with high accuracy.

Moreover, it is more preferable in the radiation detector signal processor that the specified number of light spread is obtained by detecting self-radiation from the scintillator with each of the light detecting elements.

Operation and Effect

The above is a concrete construction of the radiation signal processor according to the present invention. As noted above, the specified number of light spread is obtained by detecting self-radiation from the scintillator. This achieves obtainment of light spread within the scintillator with high accuracy.

Moreover, it is more preferable in the radiation detector signal processor that the spectrum obtaining device, the peak value obtaining device, and the variation obtaining device cooperate to receive the detection data and obtain the variation alternately and repeatedly.

Operation and Effect

The above is a concrete construction of the radiation signal processor according to the present invention. The variation is obtained and then the radiation detector is controlled. Thereafter detection data is again obtained, and then a new variation is obtained in accordance with the detection data. Accordingly, the variation obtained after the variation initially obtained indicates a difference in fluorescence detection sensitivity of the light detecting elements more accurately than that obtained initially.

The specification of the present invention also includes a disclosure concerning to a radiation detector with a function of the above radiation detector signal processor. That is, another aspect of the present invention discloses a radiation detector including a scintillator configured to convert radiation into fluorescence; a plurality of light detecting elements each configured to detect an intensity of the fluorescence; an amplifying device configured to amplify signals from the light detecting elements; a spectrum obtaining device configured to receive detection data from the amplifying device for obtaining an energy spectrum of radiation corresponding to the detection data for each of the light detecting elements; a peak value obtaining device configured to obtain a peak value of the energy spectrum for each of the light detecting elements; and a variation obtaining device configured to obtain a variation in fluorescence detection intensity among the light detecting elements in accordance with the peak value and a specified number of light spread, thereby determining an amplification factor of the amplifying device, the light spread indicating how the fluorescence generated in the scintillator spreads spatially until reaching each of the detecting elements.

Moreover, it is more preferable in the radiation detector that the specified number of light spread is obtained by emitting the radiation uniformly to the scintillator and detecting the radiation with each of the light detecting elements.

Moreover, it is more preferable in the radiation detector that the specified number of light spread is obtained by detecting self-radiation from the scintillator with each of the light detecting elements.

Moreover, it is more preferable in the radiation detector signal processor that the spectrum obtaining device, the peak value obtaining device, and the variation obtaining device cooperate to receive the detection data and obtain the variation alternately and repeatedly.

Operation and Effect

In the radiation detector according to the aspect of the present invention, the variation in fluorescence detection intensity among the light detecting elements is obtained and an amplification factor of the signals is changed to cancel the variation. With the construction of the present invention, the variation is obtainable in accordance with the detection data (the peak value) of the fluorescence and the specified number of light spread indicating how the fluorescence generated in the scintillator spreads spatially until reaching each of the detecting elements. Such a construction allows accurate obtainment of the variation in the radiation detector in which the fluorescence is detected with a plurality of light detecting elements while spreading. The amplification factor is determined in accordance with the variation, achieving more accurate positional identification by the radiation detector.

Advantageous Effects of Invention

The radiation detector signal processor according to the present invention obtains the variation in fluorescence detection intensity among the light detecting elements of the radiation detector. With the construction of the present invention, the variation is obtainable in accordance with the detection data (the peak value) of the fluorescence and the specified number of light spread indicating how the fluorescence generated in the scintillator spreads spatially until reaching each of the detecting elements. Such a construction allows accurate obtainment of the variation in the radiation detector in which the fluorescence is detected with a plurality of light detecting elements while spreading. The radiation detector is adjusted in accordance with the variation, achieving more accurate positional identification by the radiation detector.

BRIEF DESCRIPTION OF DRAWINGS

FIGS. 14 and 15 are schematic views each illustrating a pattern of fluorescence spread according to the embodiment.

FIG. 16 is a schematic view illustrating a specified number of light spread according to the embodiment.

DESCRIPTION OF EMBODIMENTS

The following describes the mode for carrying out the invention with reference to drawings.

Embodiment 1

<Whole Construction of Radiation Detector Signal Processor>

Figure 1:
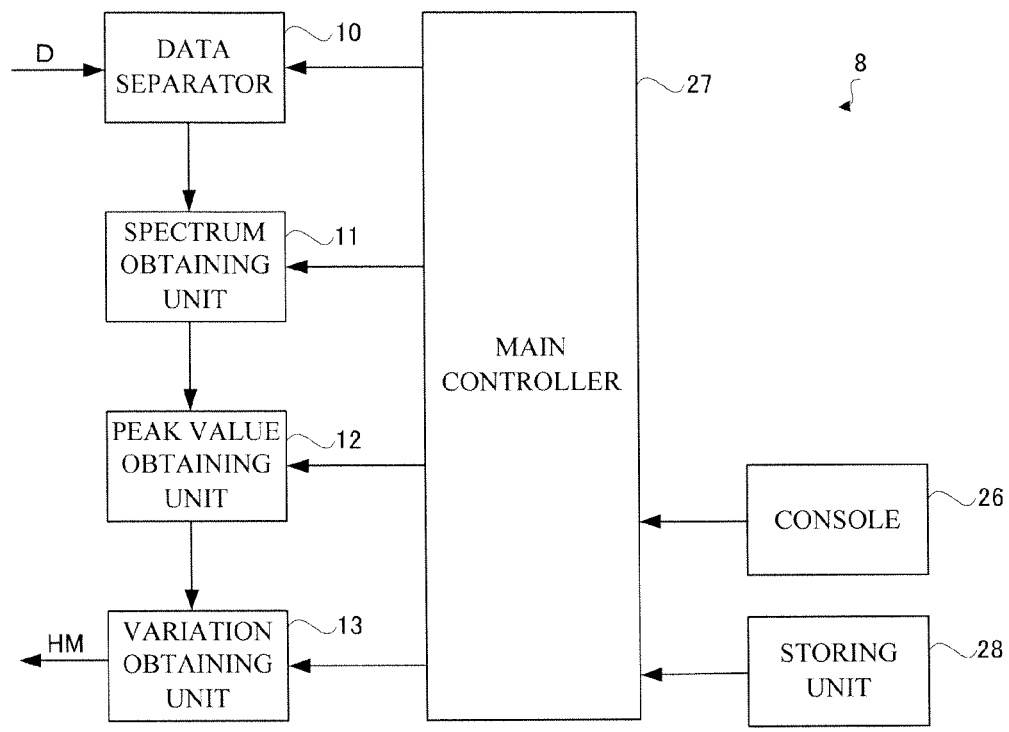
FIG. 1 is a function block diagram illustrating a radiation detector signal processor according to one embodiment.

As illustrated in FIG. 1, a radiation detector signal processor according to Embodiment 1 (hereinafter, simply referred to as a signal processor 8) receives detection data D outputted by detecting radiation with a radiation detector, and then outputs a variation map HM indicating a variation in sensitivity of the radiation detector. Here, the detection data D indicates distribution of fluorescence detected with the radiation detector.

The signal processor 8 includes a data separator 10 configured to separate the detection data D for each of light detecting elements, a spectrum obtaining unit 11 configured to obtain an energy spectrum of radiation for each of the light detecting elements 3a, a peak value obtaining unit 12 configured to obtain a peak value of the energy spectrum for each of the light detecting elements 3a, and a variation obtaining unit 13 configured to obtain a variation in fluorescence detection intensity among the light detecting elements 3a. The spectrum obtaining unit 11 corresponds to the spectrum obtaining device in the present invention. The peak value obtaining unit 12 corresponds to the peak value obtaining device in the present invention. The variation obtaining unit 13 corresponds to the variation obtaining device in the present invention.

A main controller 27 controls every controller en bloc. The main controller 27 has a CPU, and executes each section 10, 11, 12, and 13 by executing various programs. A console 26 is used for inputting instructions by an operator. A storing unit 28 stores a type map TM to which the variation obtaining unit 13 refers.

<Whole Construction of Radiation Detector>

Figure 2:
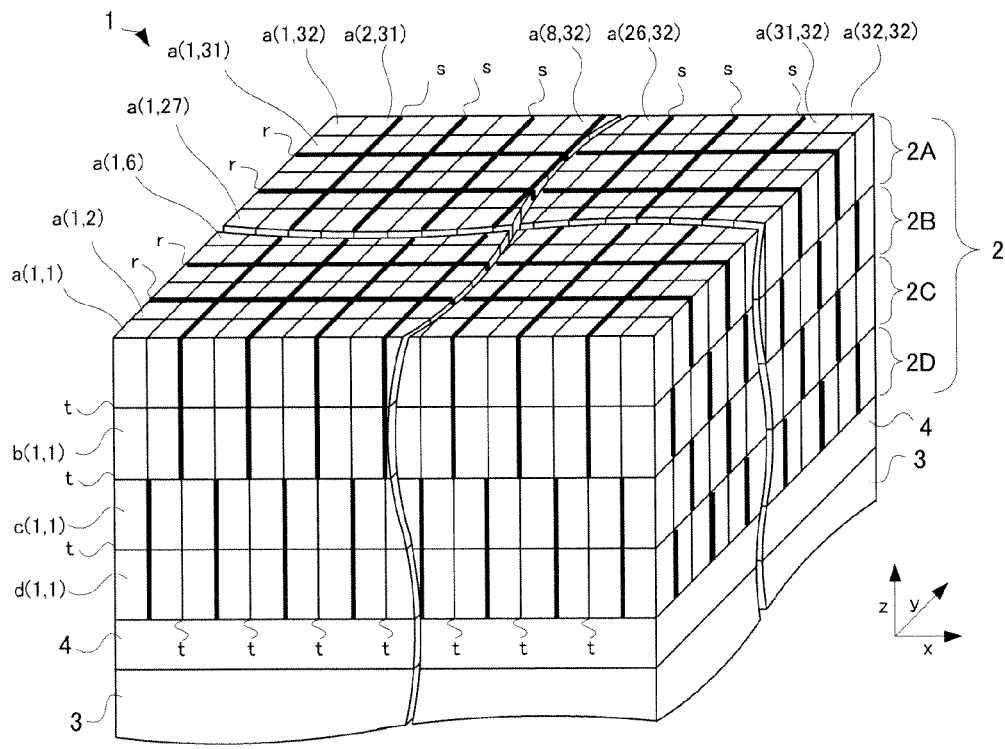
FIG. 2 is a perspective view illustrating the radiation detector according to the embodiment.

The following describes a radiation detector 1 according to Embodiment 1 prior to description about the signal processor 8 according to Embodiment 1. FIG. 2 is a perspective view of the radiation detector according to Embodiment 1. As illustrated in FIG. 2, the radiation detector 1 according to Embodiment 1 includes a scintillator 2 composed of a scintillation counter crystal layer 2D, 2C, 2B, and 2A laminated in this order in a z-direction, a photomultiplier tube (hereinafter referred to as a light detector) 3 provided on an undersurface of the scintillator 2 and having a positional identification function of detecting fluorescence emitted from the scintillator, and a light guide 4 between the scintillator 2 and the light detector 3 for receiving fluorescence. Consequently, the scintillation counter crystal layers are laminated in a direction toward the light detector 3.

The scintillator 2 is formed by scintillation counter crystals suitable for detecting γ-rays arranged three-dimensionally. Specifically, the scintillation counter crystal is composed of Ce-doped $Lu_{2(1-X)}Y_{2X}SiO_5$ (hereinafter, referred to as LYSO). Each of the scintillation counter crystals is, for example, a rectangular solid having a length of 1.45 mm in the x-direction, a width of 1.45 mm in the y-direction, and a height of 4.5 mm, regardless of the scintillation counter crystal layer. The scintillator 2 has four side end faces that are covered with a reflective film not shown.

The scintillator 2 includes four scintillation counter crystal layers 2A, 2B, 2C, and 2D. The scintillation counter crystal layers 2A, 2B, 2C, and 2D are optically coupled to one another, and a transparent material t is provided between two of the layers. A thermosetting resin composed of a silicone resin may be used for the transparent material t.

The scintillation counter crystal layer 2A corresponds to a light receiver of gamma-rays emitted from a radioactive source. Block scintillation counter crystals are arranged in a two-dimensional array. That is, 32 scintillation counter crystals are arranged in an x-direction and 32 scintillation counter crystals are arranged in a y-direction with respect to a scintillation counter crystal a (1, 1). That is, the scintillation counter crystals a (1, 1) to a (1, 32) are arranged in the y-direction to form a scintillation counter crystal array. The 32 scintillation counter crystal arrays are arranged in the x-direction to form the scintillation counter crystal layer 2A.

Here, as for the scintillation counter crystal layers 2B, 2C, and 2D, 32 scintillation counter crystals and 32 scintillation counter crystals are also arranged in the x-direction and the y-direction in a matrix in a two-dimensional array with respect to a scintillation counter crystal b (1, 1), c (1, 1), and d (1, 1), respectively. In each of the scintillation counter crystal layers 2A, 2B, 2C, and 2D, the transparent material t is also provided between the scintillation counter crystals adjacent to each other. Consequently, each of the scintillation counter crystals is to be enclosed with the transparent material t. The transparent material t has a thickness of around 25 μm.

The following describes a reflector. First reflectors r extending in the x-direction and second reflectors s extending in the y-direction are provided in the scintillation counter crystal layers 2A, 2B, 2C, and 2D, respectively, provided in the scintillator 2. Both reflectors r and s are inserted in gaps between the arranged scintillation counter crystals.

Figures 3, 4:
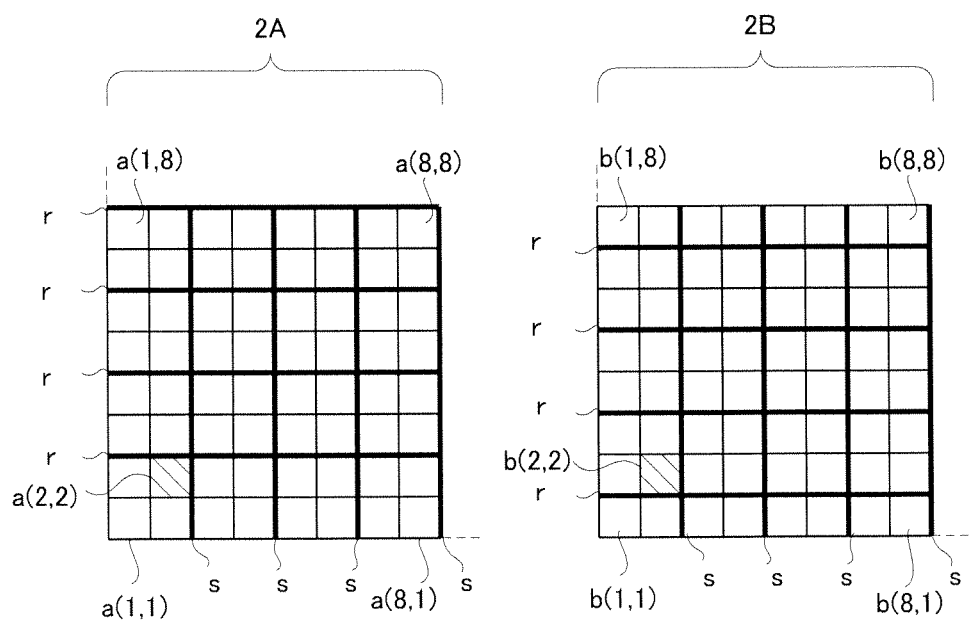
FIG. 3 is a plan view illustrating light detecting elements according to the embodiment.
FIGS. 4 and 5 are plan views each illustrating positional identification in a depth direction according to the embodiment.

FIG. 3 illustrates a light detector 3. The light detector 3 is multi-anode type, and allows identification of positions of incident fluorescence in x- and y-directions. A coupling portion of the light detector 3 to the light guide 4 includes light detecting elements 3a arranged in an 8 by 8 two-dimensional matrix. The light detecting element 3a has an amplifier for detection signals. Changing an amplification factor of the amplifier allows adjusting a sensitivity of the light detecting element 3a.

<Identification of Generating Position of Fluorescence>

Figure 5:
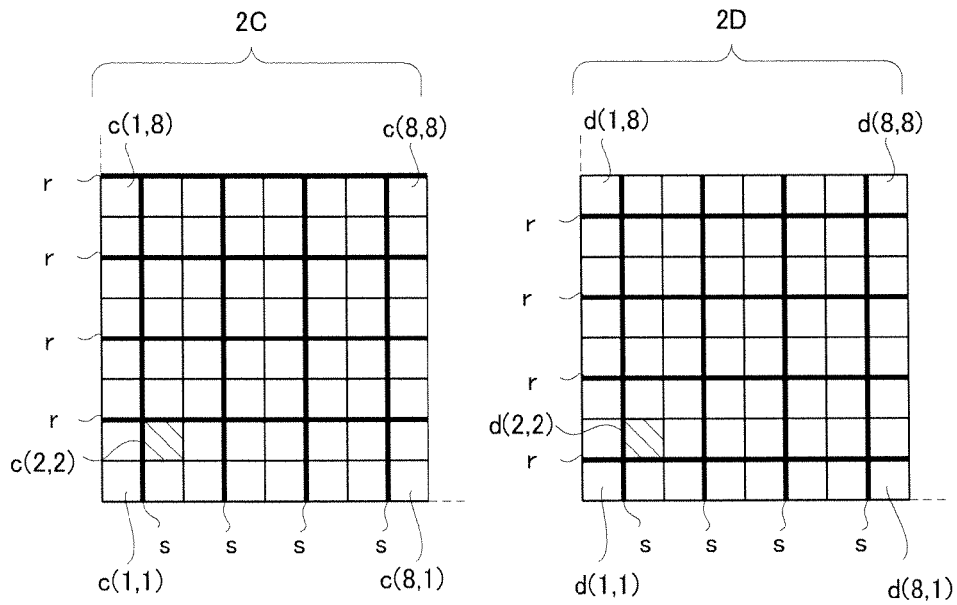

The following describes positional identification of fluorescence in the z-direction of the radiation detector 1 according to Embodiment 1. As illustrated in FIGS. 4 and 5, the first reflector r differs from the second reflector s in inserting position in each of the scintillation counter crystal layers 2A, 2B, 2C, and 2D that constitute the scintillator 2. Here, FIGS. 4 and 5 each illustrates one end of the scintillator 2 according to Embodiment 1. FIG. 4 illustrates the scintillation counter crystal layers 2A and 2B on the left and right thereof, respectively. FIG. 5 illustrates the scintillation counter crystal layers 2C and 2D on the left and right thereof, respectively.

Four scintillation counter crystal a(2,2), b(2,2), c(2,2), d(2,2) located at (2,2) all have two adjacent sides covered with the reflectors. In addition, the scintillation counter crystals located at (2,2) have the reflectors whose directions are different from one another. Thus, the four scintillation counter crystals a(2,2), b(2,2), c(2,2), and d(2,2) having the same position in the x- and y-directions each have different optical conditions.

Accordingly, the fluorescence generated in the scintillation counter crystal reaches the light detector 3 while spreading in the x- and y-directions. Provision of the reflector gives an orientation to the spreading of the fluorescence. Moreover, the fluorescence generated in the four scintillation counter crystals located at the same position in the x- and y-directions differs from one another in a spreading direction. In other words, a difference in generating position of fluorescence in the z-direction of the scintillator 2 is converted into a difference in position of the fluorescence in the x- and y-directions. The light detector 3 detects a slight variation of the fluorescence in the x- and y-direction derived from such the difference in position in the z-direction. Then a generating position of fluorescence in the z-direction can be calculated.

<Concrete Construction of Radiation Detector Signal Processor>

The following describes a concrete construction of the signal processor 8. When a position of the radiation detector 1 is adjusted with use of the signal processor 8, radiation is firstly emitted to the radiation detector 1 uniformly. Then, fluorescence is generated from each of the scintillation counter crystals evenly to be detected with the light detector 3.

<Regarding Two-Dimensional Map>

Figure 6:
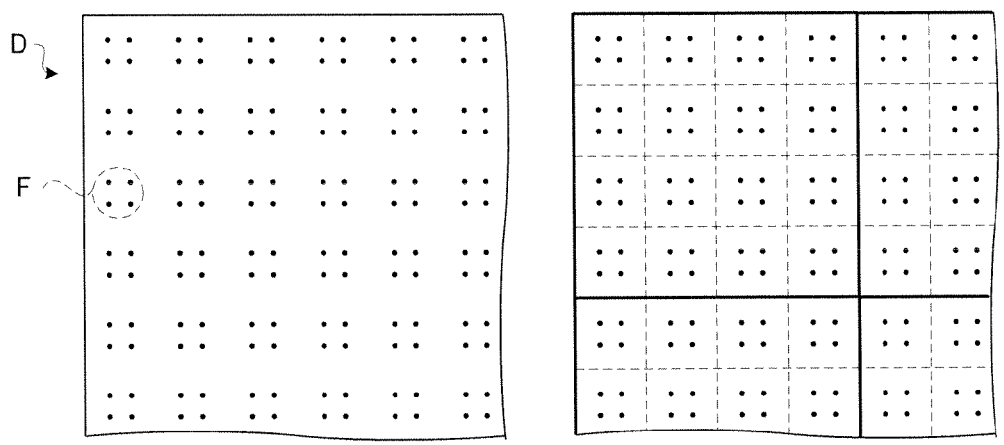
FIG. 6 is a schematic view illustrating detection data according to the embodiment.

At this time, the signal processor 8 receives detection data D in the form of a two-dimensional map in FIG. 6 from the radiation detector 1. As illustrated on the left of FIG. 6 briefly, the two-dimensional map has segments F each composed of four dots of 2 by 2 in row and column. The segments F are arranged in a two-dimensional matrix. One segment F corresponds to one scintillation counter crystal. Consequently, 32 by 32 segments F are arranged in a matrix on the two-dimensional map.

The segment F is composed of four dots. Each dot indicates fluorescence emitted from a different scintillation counter crystal. The fluorescence appears at different positions although four scintillation counter crystals are located at the same position on the detecting surface of the light detector 3. This is because the scintillator 2 includes the reflectors r and s. The principle of different positions of fluorescence has already been described with FIGS. 4 and 5.

The two-dimensional map may be divided as illustrated on the right of FIG. 6. In the drawing, dotted line indicates division of the two-dimensional map for every scintillation counter crystal. The two-dimensional map is divided for each four dots by the dotted lines. In the drawing, a bold frame indicates division of the two-dimensional map for each light detecting elements 3a of the light detector 3. The two-dimensional map is divided for each an 8 by 8 two-dimensional array by the bold frame.

<Distortion of Two-Dimensional Map>

Figure 7:
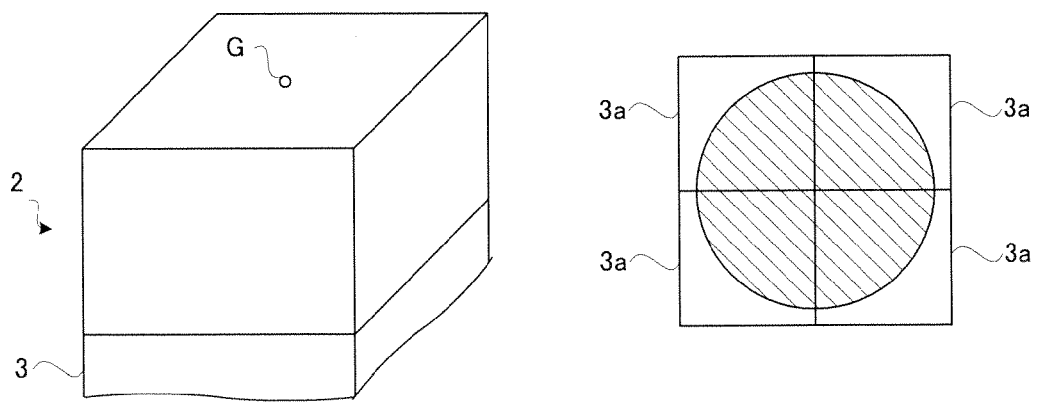
FIGS. 7 to 9 are schematic views each illustrating a reason why detection positions deviate according to the embodiment.

FIG. 6 illustrates the dots each arranged regularly. This condition is ideal. However, dots in an actual two-dimensional map are arranged distortedly. The following describes the reason for this. FIG. 7 illustrates on the left thereof a virtual radiation detector provided for describing the reason for the distorted arrangement. It is assumed that a scintillator 2 is composed of a single scintillation counter crystal, and a light detector 3 receiving fluorescence includes four light detecting elements 3a in a 2 by 2 matrix array.

Then it is assumed that fluorescence is generated from a position G illustrated on the left of FIG. 7. Here, the position G is the center of the light detector 3. The fluorescence generated from the position G enters into the four light detecting elements 3a uniformly while gradually spreading. FIG. 7 illustrates on the right thereof incidence of the fluorescence to each of the light detecting elements 3a with diagonally shaded areas.

Figure 8:
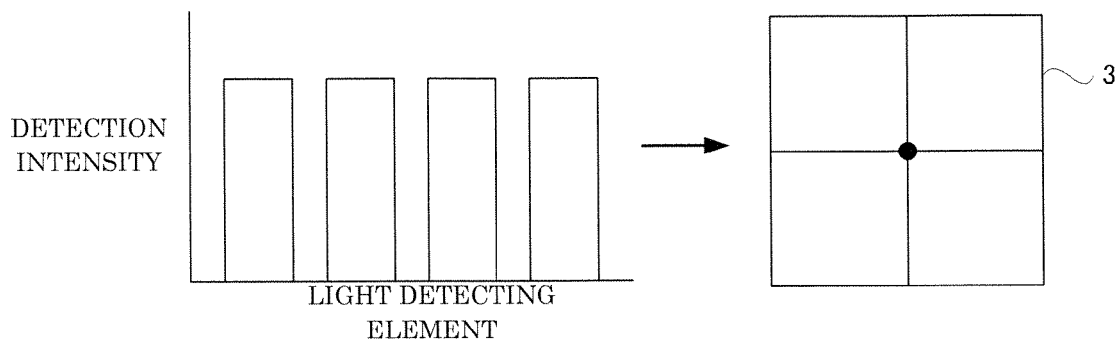

FIG. 8 illustrates the case when the light detecting elements 3a have a uniform fluorescence detecting property. At this time, as illustrated in FIG. 8 with a bar graph, the light detecting elements 3a have a uniform output fluorescence intensity. Accordingly, it is identified that a generating position of fluorescence is the center of the light detector 3 as illustrated on the right of the drawing. In this manner, the generating position of fluorescence can be identified accurately in the case of FIG. 8.

Figure 9:
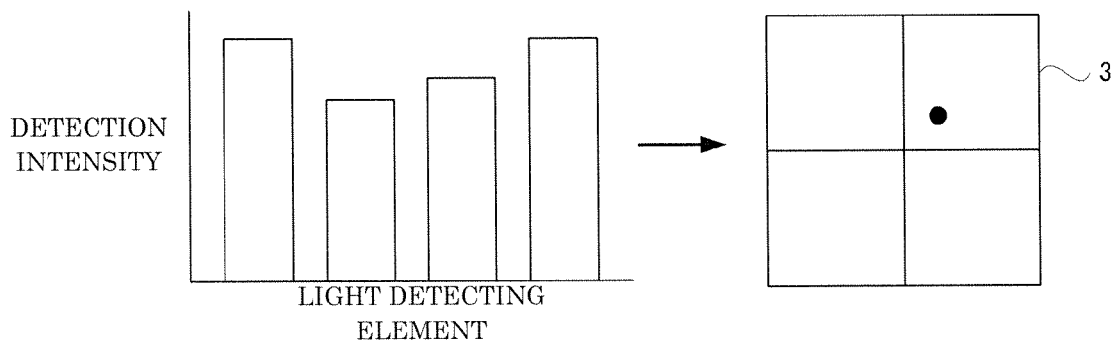

FIG. 9 illustrates the case when the light detecting elements 3a have a variation in fluorescence detecting property. At this time, as illustrated in FIG. 9 with a bar graph, the light detecting elements 3a have different output fluorescence intensities. Accordingly, it is identified that a generating position of fluorescence is out of the center of the light detector 3 as illustrated on the right of the drawing. Specifically, it is identified that the generating position of fluorescence is shifted from the center of the light detector 3 toward a light detecting elements 3a detecting a higher fluorescence intensity. As noted above, in the case of FIG. 9, the generating position of fluorescence cannot be identified with high accuracy.

That is, when the light detecting elements 3a have different fluorescence detecting properties, the generating position of fluorescence is shifted from an actual generating position. Since the actual light detecting elements 3a have different fluorescence detecting properties, the generating position of fluorescence cannot be identified accurately with the detection data D (two-dimensional map) outputted from the radiation detector.

<Operation of Data Separator>

When receiving the detection data D, the data separator 10 separates the detection data D for each of the light detecting elements 3a. Specifically, the data separator 10 divides the two-dimensional map in FIG. 6 by an 8 by 8 lattice pattern into 64 pieces of data. Then, the data separator 10 transmits the divided pieces of data to the spectrum obtaining unit 11.

<Operation of Spectrum Obtaining Unit>

Figure 10:
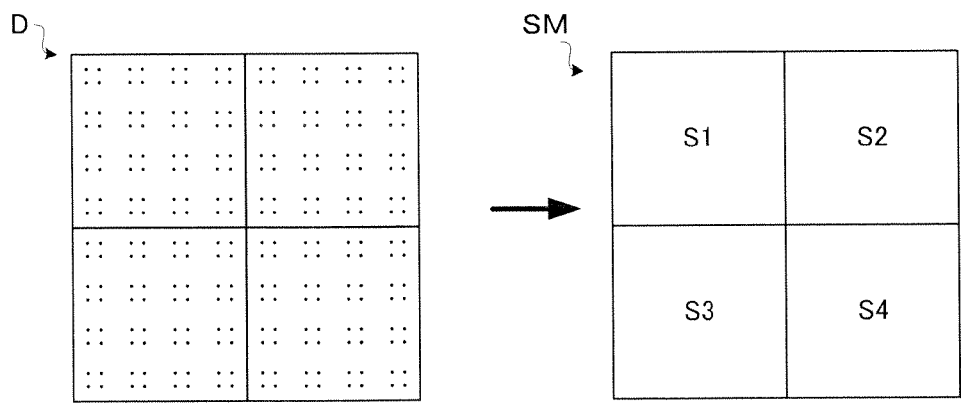
FIGS. 10 and 11 are schematic views each illustrating a spectrum data map according to the embodiment.

The spectrum obtaining unit 11 generates an energy spectrum of radiation for each of the light detecting elements 3a in accordance with the divided 64 pieces of data. Accordingly, the 64 pieces of data generated by the data separator 10 are converted into 64 pieces of spectrum data. FIG. 10 illustrates operation of the data separator 10 and the spectrum obtaining unit 11. The data separator 10 and the spectrum obtaining unit 11 cooperate to generate a spectrum data map SM from the detection data D with each the spectrum data is mapped in accordance with the position of each of the light detecting elements 3a. FIG. 10 illustrates only four light detecting elements 3a and thus four pieces of spectrum data S1 to S4 arranged for illustration purposes. However, an actual spectrum data SP contains 64 pieces of spectrum data S1 to S64 arranged in an 8 by 8 two-dimensional matrix.

Figure 11:
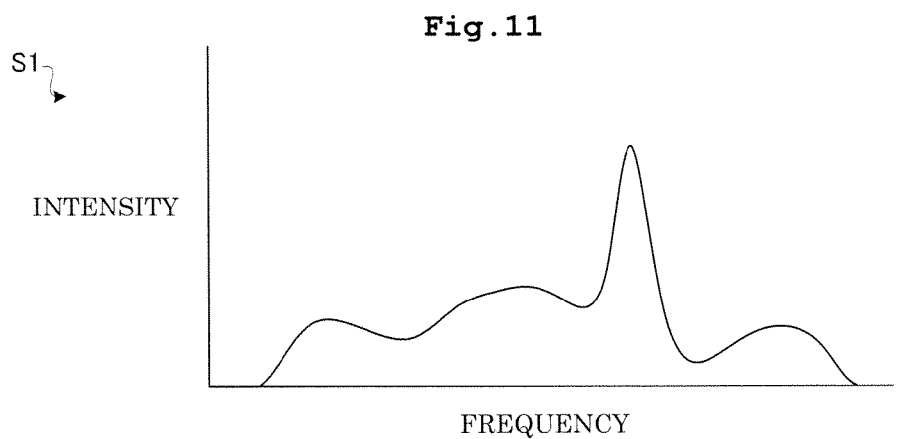

FIG. 11 illustrates the spectrum data S1 concretely. The spectrum data S1 has a relationship between a frequency and an intensity, and expresses energy distribution of detected radiation. The spectrum data S1 has a peak appearing therein. This is because the radiation detected by the radiation detector is generated from a specific nuclide radioactive material.

<Operation of Peak Value Obtaining Unit>

Figure 12:
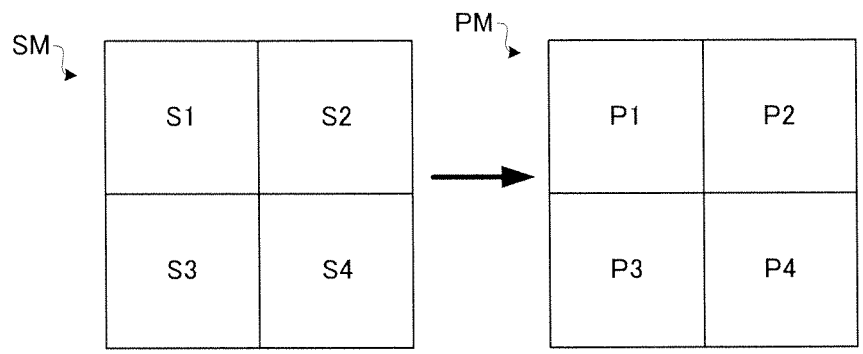
FIGS. 12 and 13 are schematic views each illustrating a peak value map according to the embodiment.

The spectrum data map SM is transmitted to the peak value obtaining unit 12. The peak value obtaining unit 12 analyzes each spectrum data constituting the spectrum data map SM to obtain peak values. Here, the peak value is a peak intensity in the spectrum data. Each the peak values are rearranged according to the spectrum data map SM, whereby a peak value map PM is generated. FIG. 12 illustrates operation of the peak value obtaining unit 12. FIG. 12 illustrates only four light detecting elements 3a and thus four peak values P1 to P4 arranged for illustration purposes. Each spectrum data S1 to S64 have the same peak frequency.

Figure 13:
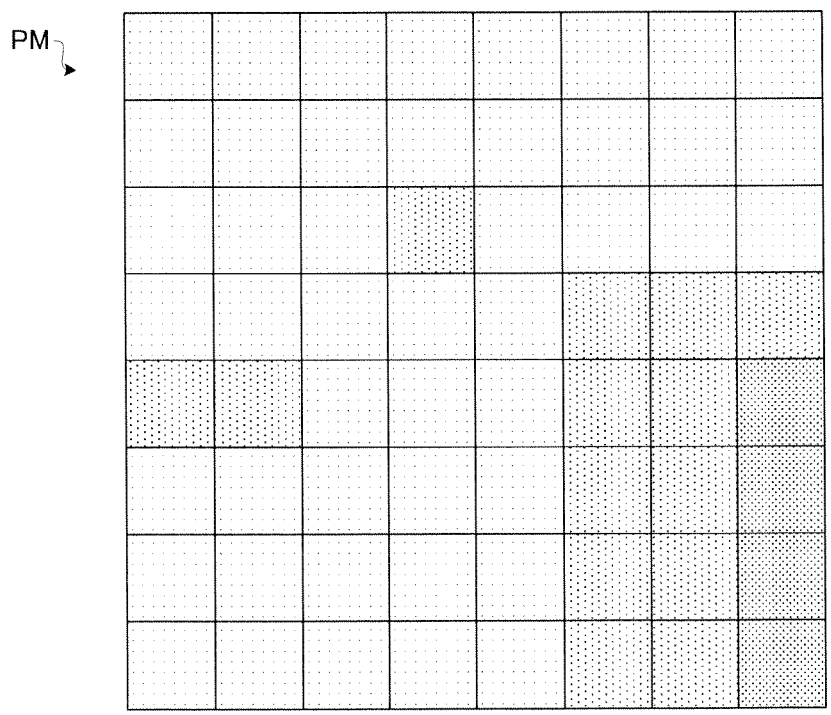

FIG. 13 illustrates an actual peak value map PM. In the actual peak value map PM, 64 peak values are arranged in an 8 by 8 two-dimensional matrix. FIG. 13 illustrates the peak value with hatches. As is seen from FIG. 13, the peak values PM are different among the light detecting elements 3a. The peak value map PM contains some portions with dense hatches. Such a portion has higher peak value than the other portions.

A variation in peak values indicates a variation in detection sensitivity of the light detecting elements 3a. It is desirable to use the peak value of the spectrum for determining the variation in detection sensitivity. Since the peak value is high in the spectrum, the detection sensitivity can be compared accurately with no obstruction of noises in the spectrum.

The variation in peak value does not directly correspond to the variation in detection sensitivity of the light detecting elements 3a. This is because the fluorescence generated in the scintillator is detected with a plurality of light detecting elements 3a. For instance, it is assumed that a radiation detector exists that fluorescence generated in a scintillator is detected with a single light detecting element 3a of the light detector 3. In this case, the peak value map PM directly indicates a variation in detection sensitivity of the light detecting element 3a. However, Embodiment 1 does not have such a construction. That is, fluorescence travels to the light detector 3 while spatially spreading, and then is detected with a plurality of light detecting elements 3a. The fluorescence spread differs depending on the position of scintillator 2. Accordingly, the peak value map PM contains a component of the variation in detection sensitivity and a component of difference of the fluorescence spread. The variation in detection sensitivity cannot be determined accurately without cancelling the component concerning the fluorescence spread from the peak value map PM.

Thus, the embodiment adopts the construction that the component of the fluorescence spread is cancelled from the peak value map PM. The following describes three patterns of the fluorescence spread depending on the positions of the light detecting elements 3a before the above construction is described.

<Pattern 1: Type α>

Firstly, attention is focused on a portion around the center of the scintillator 2. When fluorescence is emitted from the scintillation counter crystal located at this position, the fluorescence travels to the light detector 3 while spreading radially. Then, the fluorescence is detected with a plurality of light detecting elements 3a around the generating position of fluorescence. FIG. 14 illustrates this condition. The fluorescence generated from the generation position G is detected with a light detecting element 3a immediately below and eight light detecting elements 3a surrounding this element. In the drawing, an area where the fluorescence reaches is denoted by a symbol R. Such fluorescence spread is referred to as a Type α.

<Pattern 2: Type β>

Next, attention is focused on a side portion of the scintillator 2. When fluorescence is emitted from a scintillation counter crystal located at this position, the fluorescence travels toward the light detector 3 while spreading radially. However, a part of the fluorescence cannot spread radially because being blocked by the reflective films provided at the side portion of the scintillator 2. Meanwhile, the fluorescence reaches the light detector 3 to be detected with a plurality of light detecting elements 3a adjacent to the fluorescence generation position. FIG. 15 illustrates this condition on the left thereof. The fluorescence generated from the generating position G is detected with the light detecting elements 3a immediately below and five light detecting elements 3a surrounding the element. In the drawing, an area where the fluorescence reaches is denoted by a symbol R, and the reflective film is indicated by a thick line. Such fluorescence spread is referred to as a Type β.

<Pattern 3: Type γ>

Finally, attention is focused on a vertex of the scintillator 2. When fluorescence is emitted from a scintillation counter crystal located at this position, the fluorescence travels toward the light detector 3 while spreading radially. However, the fluorescence mostly cannot spread radially because being blocking by the two reflective films provided at two sides of the scintillator 2. Meanwhile, the fluorescence reaches the light detector 3 to be detected with a plurality of light detecting elements 3a adjacent to the fluorescence generation point. FIG. 15 illustrates this condition on the right thereof. The fluorescence generated from the generating position G is detected with the light detecting elements 3a immediately below and three light detecting elements 3a surrounding the element. In the drawing, an area where the fluorescence reaches is denoted by a symbol R, and the reflective film is indicated by a thick line. Such fluorescence spread is referred to as a Type γ.

FIG. 16 illustrates actual measurement of the fluorescence spread in each of the patterns. FIG. 16 illustrates what percent of fluorescence reaches each of the light detecting elements 3a when the fluorescence is generated immediately above the light detecting elements 3a diagonally shaded. The fluorescence spread is obtainable by actually emitting radiation to the radiation detector uniformly. Virtual fluorescence spread is applied to the detection data D detected at this time, and then it is determined whether or not a fluorescence intensity detected with each of the light detecting elements 3a corresponds to this. Such detection and determination of radiation is repeated, whereby suitable fluorescence spread is obtained. A value that specified the fluorescence spread is a specified number of light spread indicating how the fluorescence generated in the scintillator 2 spreads spatially until reaching the light detecting elements 3a.

<Operation of Variation Obtaining Unit>

Figure 17:
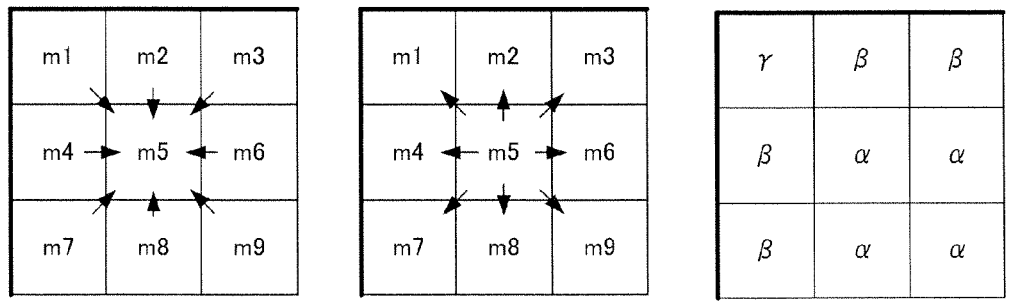
FIGS. 17 to 21 are schematic views each illustrating obtaining a variation in fluorescence sensitivity according to the embodiment.

The peak value map PM is transmitted to the variation obtaining unit 13. The variation obtaining unit 13 obtains a variation in fluorescence detection intensity among the light detecting elements 3a using the specified number of light spread and the peak value map PM. The following describes a concrete obtaining method of the variation. FIG. 17 illustrates a light detecting element m5. Then, fluorescence incident into the light detecting element m5 is to be described in detail.

Firstly, it is conceivable that fluorescence generated immediately above the light detecting element m5 (a portion immediately above m5) in the scintillator 2 enters into the light detecting elements m5. On the other hand, this is not only the fluorescence entering into the light detecting element m5. Here, light detecting elements m1, m2, m3, m4, m6, m7, m8, and m9 surrounding the light detecting element m5 should be regarded. That is, a part of fluorescence generated from immediately above portions of the light detecting elements m1, m2, m3, m4, m6, m7, m8, m9 in the scintillator 2 (portions immediately above m1, m2, m3, m4, m6, m7, m8, m9) enters into the light detecting element m5, as illustrated on the left of FIG. 17.

In addition, all the fluorescence generated from the portion immediately above m5 in the scintillator 2 does not enter into the light detecting element m5. That is, a part of the fluorescence generated from the portion immediately above m5 in the scintillator 2 spreads from a detection area of the light detecting element m5 to enter into the light detecting elements m1, m2, m3, m4, m6, m7, m8, m9.

That is, the fluorescence incident into the light detecting element m5 decreases by the fluorescence flowing into the other light detecting elements and increases by the fluorescence flowing from the other light detecting elements. Under this assumption, it is expected that an inflow of the fluorescence is equal to an outflow of the fluorescence. However, this is not so since the fluorescence spread within the scintillator 2 varies depending on the positions of the light detecting elements 3a. Specifically, the fluorescence spread within the scintillator 2 includes three patterns, namely Types α, β, γ, depending on the positions of the light detecting elements 3a. See the right of FIG. 17. In the drawing, the thick line indicates the side of the scintillator 2.

Figure 18:
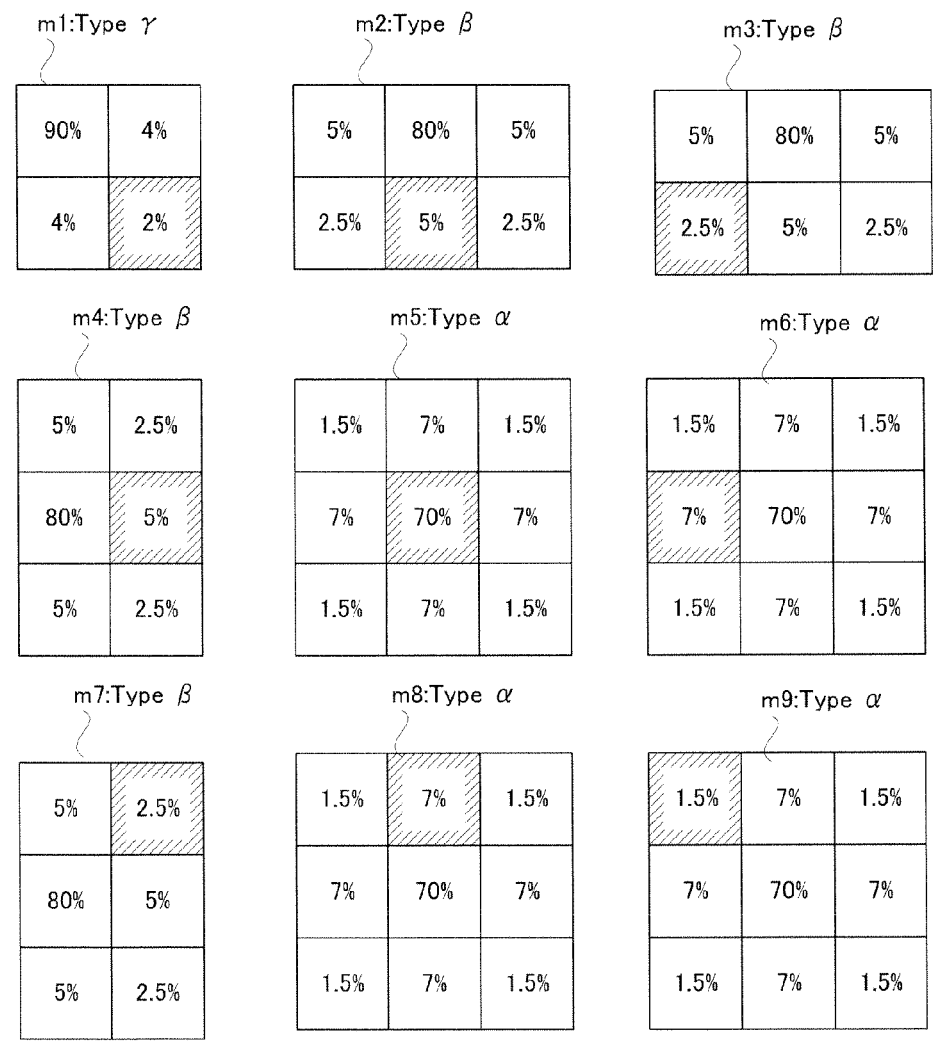

FIG. 18 illustrates fluorescence incident into the light detecting element m5. The diagonally shaded element in FIG. 18 indicates the light detecting element m5. The fluorescence generated in the scintillation counter crystal immediately above the light detecting element m1 spreads by a pattern Type γ, and 2% of the total fluorescence enters into the light detecting element m5. Similarly, the fluorescence generated in the scintillation counter crystals immediately above the light detecting elements m2 and m4 spreads by a pattern Type β, and 5% of the total fluorescence enters into the light detecting elements m5. The fluorescence generated in the scintillation counter crystals immediately above the light detecting elements m3 and m7 spreads by a pattern Type β, and 2.5% of the total fluorescence enters into the light detecting element m5. The fluorescence generated in the scintillation counter crystals immediately above the light detecting elements m6 and m8 spreads by a pattern Type α, and 7% of the total fluorescence enters into the light detecting element m5. The fluorescence generated in the scintillation counter crystal immediately above the light detecting element m9 spreads by a pattern Type α, and 1.5% of the total fluorescence enters into the light detecting element m5. The fluorescence generated in the scintillation counter crystal immediately above the light detecting element m5 spreads by a pattern Type α, and 70% of the total fluorescence enters into the light detecting element m5.

Here, numerals b1 to b9 are given to detection intensities of fluorescence generated in the scintillation counter crystals immediately above the light detecting elements m1 to m9 in FIG. 19, respectively, that are detected with the light detecting elements m1 to m9 immediately below the scintillation counter crystals. The detection intensities b1 to b9 each indicate a detection intensity at the peak value. Accordingly, a detection intensity S(m5) at a peak value of the fluorescence detected with the light detecting elements m5 can be expressed by the following equation. The detection intensity S(m5) is a detection intensity of the fluorescence actually measurable. That is, the detection intensity S(m5) differs from the detection intensity b1 to b9 that are not actually measurable.

$$S(m5)=b1\times 2\%+b2\times 5\%+b3\times 2.5\%+b4\times 5\%+b5\times 70\%+b6\times 7\%+b7\times 2.5\%+b8\times 7\%+b9\times 1.5\%$$

Similarly, a detection intensity S(m1) can be expressed by the detection intensities b1, b2, b4, b5 and the specified number of light spread. A detection intensity S(m2) can be expressed by the detection intensities b1, b2, b3, b4, b5, b6 and the specified number of light spread. Moreover, a detection intensity S(m3) can be expressed by the detection intensities b2, b3, b5, b6, and the specified number of light spread. A detection intensity S(m4) can be expressed by the detection intensities b1, b2, b4, b5, b7, b8 and the specified number of light spread. Similarly, a detection intensity S(m6) can be expressed by the detection intensities b2, b3, b5, b6, b8, b9, and the specified number of light spread. A detection intensity S(m7) can be expressed by the detection intensities b4, b5, b8, and the specified number of light spread. A detection intensity S(m8) can be expressed by the detection intensities b4, b5, b6, b7, b8, b9, and the specified number of light spread. A detection intensity S(m9) can be expressed by the detection intensities b5, b6, b8, b9, and the specified number of light spread. In other words, the detection intensity S of the light detecting element can be expressed with the detection intensities b1 to b9 corresponding to the light detecting elements adjacent to the light detecting element and the specified number of light spread.

As noted above, simultaneous equations are obtainable that are formed by nine different equations about the detection intensities S(m1) to S(m9). Since the detection intensities S(m1) to S(m9) are known from the peak value map PM, solving the simultaneous equations for the intensities b1 to b9 can achieve determination of the intensities b1 to b9.

The intensities b1 to b9 obtained in this manner should have the same value. This is because uniform incidence of radiation into the scintillator 2 causes uniform detection intensity of fluorescence independently of the light detecting elements. In actual, however, the intensities b1 to b9 are not uniform. This is because the fluorescence detection sensitivity varies among the light detecting elements. In other words, the intensities b1 to b9 directly corresponds to the variations in fluorescence sensitivity.

The variation obtaining unit 13 outputs the obtained variation b5 to the radiation detector. Here, variations other than the variation b5 obtained from the simultaneous equations are not outputted. The following describes how the variation obtaining unit 13 obtains the variations other than that of the light detecting element m5. For instance, for obtaining a variation b1 of the light detecting elements m1, simultaneous equations are prepared again in accordance with the peak values of the light detecting elements m2, m3, m4 surrounding the light detecting element m1 and the specified number of light spread. Then, the variation b1 is determined based on the simultaneous equations. Other variations of the light detecting elements 3a are determined in such a manner. At this time, the variation obtaining unit 13 refers to a type map TM indicating a type of fluorescence spread in the scintillation counter crystal immediately above the light detecting element. The type map TM has a correspondence between the light detecting element and the type of fluorescence spread as in FIG. 20.

The variation obtaining unit 13 calculates the variations of all the 64 light detecting elements in the light detector 3 in the same manner to obtain a variation map HM with the variations arranged two-dimensionally. The variation map HM is transmitted to the radiation detector 1. The radiation detector 1 controls an amplifier to control a gain of detection sensitivities of the light detecting elements so as to cancel the variations.

<Entire Data Processing>

Figures 19, 20, 21:
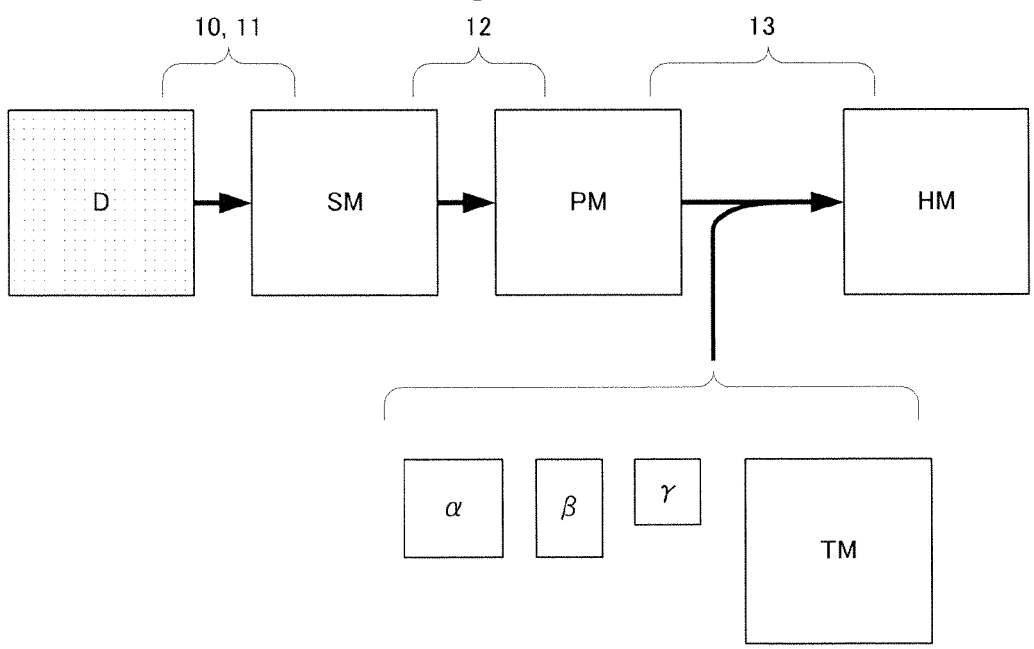

FIG. 21 schematically illustrates data processing noted above. The data separator 10 and the spectrum obtaining unit 11 generates a spectrum map SM from the detection data D outputted by detecting radiation with the radiation detector 1. The peak value obtaining unit 12 generates a peak value map PM from the spectrum map SM. Then the variation obtaining unit 13 generates a variation map HM from the peak value map PM, the type map TM, and the specified number of light spread.

As noted above, the radiation detector signal processor according to the present invention obtains the variation in fluorescence detection intensity among the light detecting elements 3a of the radiation detector 1. With the construction of the present invention, the variation is obtainable in accordance with the detection data (the peak value) of the fluorescence and the specified number of light spread indicating how the fluorescence generated in the scintillator 2 spatially spreads until reaching each of the detecting elements 3a. Such a construction allows accurate obtainment of the variation in the radiation detector 1 in which the fluorescence is detected with a plurality of light detecting elements 3a while spreading. The radiation detector 1 is adjusted in accordance with the variation, achieving more accurate positional identification by the radiation detector 1.

Moreover, as noted above, the specified number of light spread is obtained by emitting radiation to the scintillator 2 uniformly. This achieves more accurate obtainment of light spread within the scintillator.

Embodiment 2

The following describes a radiation detector according to Embodiment 2. The radiation detector in Embodiment 2 has the signal processor 8 of the Embodiment 1 embedded therein.

Figure 22:
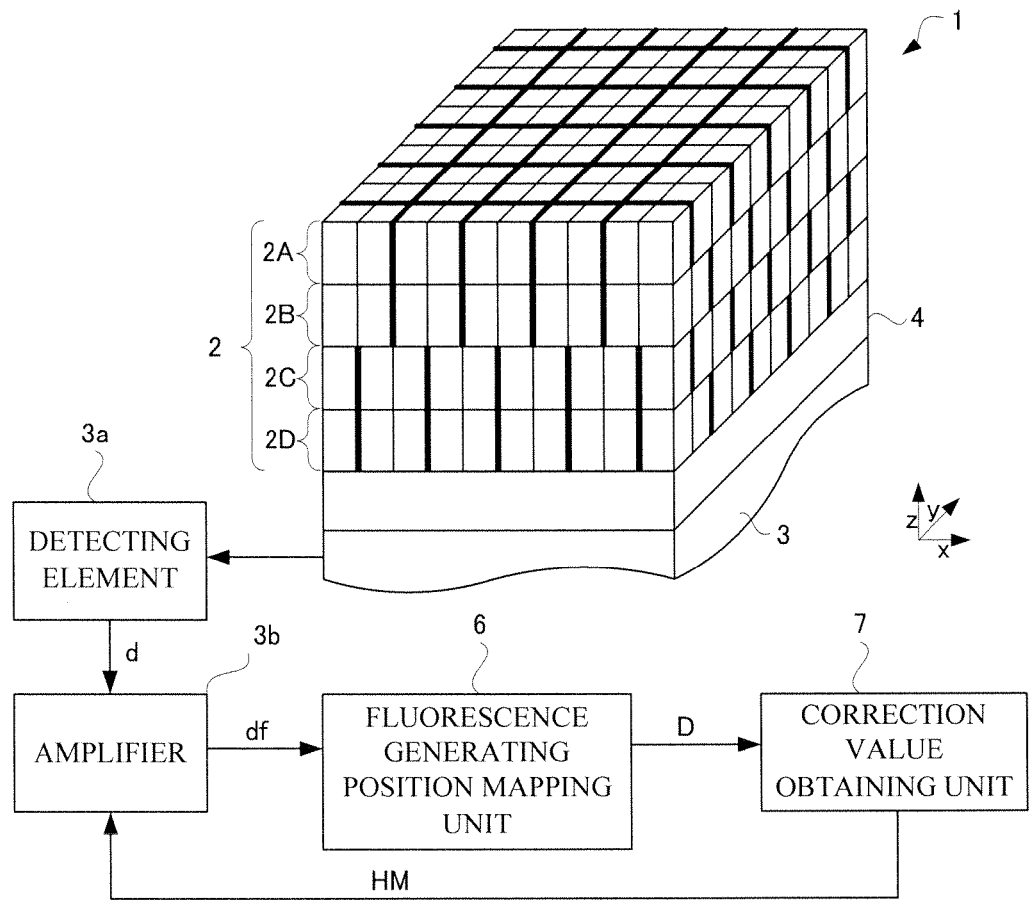
FIG. 22 is a function block diagram illustrating a radiation detector according to another embodiment.
Figure 23:
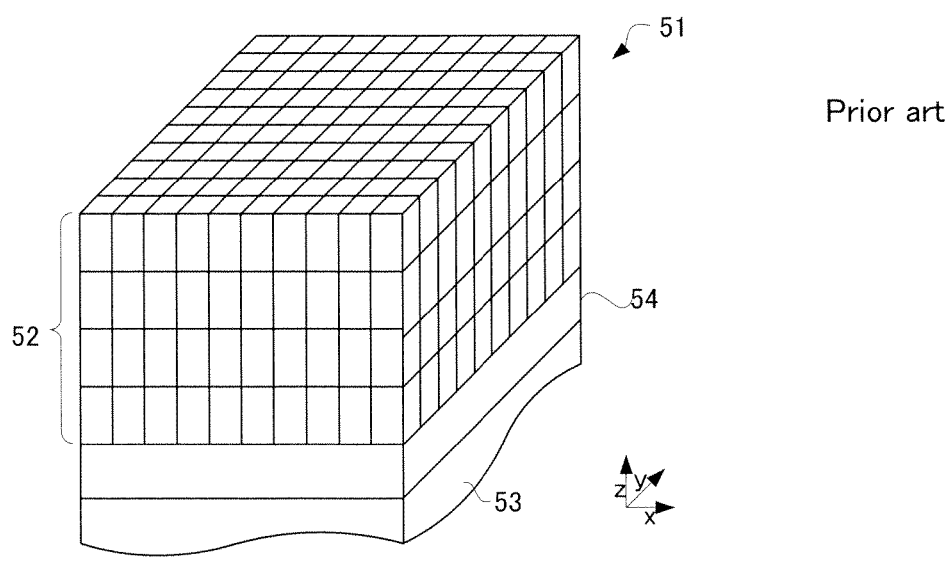
FIG. 23 illustrates a currently-used apparatus.

A construction of the radiation detector in Embodiment 2 is to be described. As illustrated in FIG. 22, the radiation detector in Embodiment 2 has the same construction as the radiation detector 1 described in Embodiment 1. Each of the light detecting elements 3a outputs original signals d to an amplifier 3b where the signals are converted into amplified signals df. A generating position of fluorescence mapping unit 6 generates a two-dimensional map, as described with FIG. 6, in accordance with the amplified signals df. The amplifier 3b is provided for each of the 64 light detecting elements 3a. The amplifier 3b corresponds to the amplifying device in the present invention.

The data separator 10, the spectrum obtaining unit 11, the peak value obtaining unit 12, and the variation obtaining unit 13 in Embodiment 1 are integrated into a correction value obtaining unit 7.

When radiation enters into the radiation detector uniformly, the generating position of fluorescence mapping unit 6 generates detection data D. The correction value obtaining unit 7 generates a variation map HM in accordance with the detection data D. The variation map HM is transmitted to the amplifier 3b. The amplifier 3b adjusts an amplification value of the signals so as to cancel the variation in fluorescence detection among the light detecting elements 3a. This cancels the variation in fluorescence detection among the light detecting elements 3a.

The radiation detector detects radiation emitted from a subject under such a condition. Since the variation in fluorescence detection among the light detecting elements 3a is cancelled at this time, the radiation detector can detect an incidence position of radiation accurately.

As noted above, the radiation detector 1 according to the present invention obtains the variation in fluorescence detection intensity among the light detecting elements 3a, and changes an amplification factor of the signals so as to cancel the variation. With the construction of the present invention, the variation is obtainable in accordance with the detection data (the peak value) of the fluorescence and the specified number of light spread indicating how the fluorescence generated in the scintillator 2 spreads spatially until reaching each of the detecting elements 3a. Such a construction allows accurate obtainment of the variation in the radiation detector 1 in which the fluorescence is detected with a plurality of light detecting elements 3a while spreading. When the amplification factor is calculated from the variation, more accurate identification in position of the radiation detector 1 is obtainable.

The present invention is not limited to the above constructions, but may be modified as under.

(1) In the above embodiments, the detection data D is obtained by emitting radiation uniformly to the scintillator 2. However, the present invention is not limited to this construction. The detection data D may be obtained by detecting self-radiation from the scintillator 2 instead of emitting radiation. With a specified number of light spread obtained by detecting self-radiation from the scintillator 2, more accurate spread of light within the scintillator is obtainable.

(2) In addition to the above constructions, the radiation detector 1 is controlled after obtaining the variation map HM and thereafter detection data is obtained again. Then, a new variation is obtained in accordance with the new detection data. Such a new variation obtained previously indicates a difference among the fluorescence detection sensitivity of the light detecting elements 3a more accurately than the variation obtained initially.

INDUSTRIAL APPLICABILITY

The present invention is suitable for a medical radiation detector signal processor and a radiation detector provided with the processor.

REFERENCE SIGN LIST 1 radiation detector
2 scintillator
3a light detecting elements
3b amplifier (amplifying device)
11 spectrum obtaining unit (spectrum obtaining device)
12 peak value obtaining unit (peak value obtaining device)
13 variation obtaining unit (variation obtaining device)

The invention claimed is:
1. A radiation detector signal processor comprising:
a spectrum obtaining device configured to receive detection data from a radiation detector provided with a scintillator and a plurality of light detecting elements, and configured to obtain an energy spectrum of radiation corresponding to the detection data for each of the light detecting elements;
a peak value obtaining device configured to obtain a peak value of the energy spectrum for each of the light detecting elements; and
a variation obtaining device configured to obtain a variation in fluorescence detection intensity among the light detecting elements in accordance with the peak value and a specified number of light spread, the specified number indicating how the fluorescence generated in the scintillator spreads spatially until reaching each of the detecting elements.

2. The radiation detector signal processor according to claim 1, wherein the specified number of light spread is obtained by emitting radiation to the scintillator uniformly and detecting the radiation with each of the light detecting elements.

3. The radiation detector signal processor according to claim 1, wherein the specified number of light spread is obtained by detecting self-radiation from the scintillator with each of the light detecting elements.

4. The radiation detector signal processor according claim 1, wherein
the spectrum obtaining device, the peak value obtaining device, and the variation obtaining device cooperate to receive the detection data and obtain the variation alternately and repeatedly.

5. A radiation detector comprising:
a scintillator configured to convert radiation into fluorescence;
a plurality of light detecting elements each configured to detect an intensity of the fluorescence;
an amplifying device configured to amplify signals from the light detecting elements;
a spectrum obtaining device configured to receive detection data from the amplifying device for obtaining an energy spectrum of radiation corresponding to the detection data for each of the light detecting elements;
a peak value obtaining device configured to obtain a peak value of the energy spectrum for each of the light detecting elements; and
a variation obtaining device configured to obtain a variation in fluorescence detection intensity among the light detecting elements in accordance with the peak value and a specified number of light spread, thereby determining an amplification factor of the amplifying device, the light spread indicating how the fluorescence generated in the scintillator spreads spatially until reaching each of the detecting elements.

6. The radiation detector according to claim 5, wherein the specified number of light spread is obtained by emitting the radiation uniformly to the scintillator and detecting the radiation with each of the light detecting elements.

7. The radiation detector according to claim 5, wherein the specified number of light spread is obtained by detecting self-radiation from the scintillator with each of the light detecting elements.

8. The radiation detector according to claim 5, wherein
the spectrum obtaining device, the peak value obtaining device, and the variation obtaining device cooperate to receive the detection data and obtain the variation alternately and repeatedly.

* * * * *